United States Patent
Nabeshima et al.

(10) Patent No.: US 10,471,038 B2
(45) Date of Patent: Nov. 12, 2019

(54) INHIBITOR OF MUSCLE DAMAGE OR MUSCLE FATIGUE

(71) Applicant: PRODUCTIVE AGING LABORATORY, CO., LTD., Osaka (JP)

(72) Inventors: Yo-ichi Nabeshima, Osaka (JP); Chiaki Abe, Osaka (JP); Yoshihiro Uto, Osaka (JP); Ryuji Hiramatsu, Osaka (JP)

(73) Assignee: PRODUCTIVE AGING LABORATORY, CO., LTD., Osaka (JP)

( * ) Notice: Subject to any disclaimer, the term of this patent is extended or adjusted under 35 U.S.C. 154(b) by 0 days.

(21) Appl. No.: 15/766,521

(22) PCT Filed: Oct. 7, 2016

(86) PCT No.: PCT/JP2016/079985
§ 371 (c)(1),
(2) Date: Apr. 6, 2018

(87) PCT Pub. No.: WO2017/061614
PCT Pub. Date: Apr. 13, 2017

(65) Prior Publication Data
US 2018/0289660 A1    Oct. 11, 2018

(30) Foreign Application Priority Data
Oct. 8, 2015 (JP) .................. 2015-200515

(51) Int. Cl.
*A61K 31/26* (2006.01)
*A61P 21/00* (2006.01)
(52) U.S. Cl.
CPC .............. *A61K 31/26* (2013.01); *A61P 21/00* (2018.01)
(58) Field of Classification Search
CPC ................................ A61K 31/26; A61P 21/00
See application file for complete search history.

(56) References Cited

U.S. PATENT DOCUMENTS

2014/0106387 A1    4/2014 Park et al.

FOREIGN PATENT DOCUMENTS

| JP | 2006-241005 A | 9/2006 |
|---|---|---|
| JP | 2009-126826 A | 6/2009 |
| JP | 2009-132635 A | 6/2009 |
| JP | 2009-526839 A | 7/2009 |
| JP | 2010-184892 A | 8/2010 |
| JP | 5824194 | * 11/2015 |
| WO | 2008060332 A2 | 5/2008 |
| WO | WO 2010086972 | * 1/2009 |
| WO | 2011076811 A1 | 6/2011 |

OTHER PUBLICATIONS

Morimitsu (JBC Papers in Press. Published on Nov. 12, 2001 as Manuscript M110244200).*
Goldstein et al. (The J. General Physiology, 136(1) 29-34 (2010).*
Whitman, S. A. et al.; "Nrf2 modulates contractile and metabolic properties of skeletal muscle in streptozotocin-induced liabetic atrophy" Experimental Cell Research, pp. 2673-2683, No. 17, Oct. 2013 (11 pages).
Extended European Search Report issued in corresponding European Patent Application No. 16853765.2 dated May 20, 2019 (8 pages).
Malaguti, M. et al.; "Sulforaphane treatment protects skeletal muscle against damage induced by exhaustive exercise in rats"; J. Appl. Physiol.; vol. 107, No. 4; Aug. 27, 2009; pp. 1028-1036 (9 pages).
Sechang, O. et al.; "Nrf2 activation remarkably improves exercise endurance capacity in mice"; Free Radical Biology and Medicine, vol. 53, Suppl 1; 2012, pp. S36-S37 (2 pages).
Sun, C. et al.; "Sulforaphane alleviates muscular dystrophy in mdx mice by activation of Nrf2"; J. Appl. Physiol., vol. 118, No. 2; 2015; pp. 224-237 (14 pages).
Sun, C. et al.; "Sulforaphane Attenuates Muscle Inflammation in Dystrophin-deficient mdx Mice via NF-E2-related Factor 2 (Nrf2)-mediated Inhibition of NF-kB Signaling Pathway"; J. Biol. Chem., vol. 290, No. 29, Jul. 17, 2015, pp. 17784-17795 (12 pages).
Elhalem, E.. et al.; "Sulforaphane homologues: Enantiodivergent synthesis of both enantiomers, activation of the Nrf2 transcription factor and selective cytotoxic activity"; Eur. J. Med. Chem., vol. 87, 2014, pp. 552-563 (12 pages).
Miller, C.J. et al.; "Disruption of Nrf2/ARE signaling impairs antioxidant mechanisms and promotes cell degradation pathways in aged skeletal muscle"; Biochimica et Biophysica Acta, vol. 1822, No. 6, 2012, pp. 1038-1050 (13 pages).
Badalamente, M. et al.; "Delay of Muscle Degeneration and Necrosis in mdx Mice by Calpain Inhibition"; Muscle & Nerve, vol. 23, No. 1, Jan. 2000, pp. 106-111 (6 pages).
Teixeira, V. et al.; "Mechanisms of muscle wasting in sarcopenia"; Ref. Bras. Reumatol., vol. 52, No. 2; 2012; pp. 247-259 (8 pages).

(Continued)

*Primary Examiner* — Shirley V Gembeh
(74) *Attorney, Agent, or Firm* — Osha Liang LLP (57) ABSTRACT

The present invention relates to a calpain activation inhibitor, muscle damage inhibitor, muscle endurance improver or muscle fatigue recovery agent containing an ω-methylsulfinylalkyl isothiocyanate or physiologically acceptable salt thereof as an active ingredient, foods or beverages, pharmaceuticals or cosmetics containing the same, a pharmaceutical for the prophylaxis and/or treatment of diseases related to muscle damage or diseases related to reduced muscle mass caused by aging, and a method for the use thereof.

4 Claims, 4 Drawing Sheets

(56) References Cited

OTHER PUBLICATIONS

Mizuno, K. et al.; "Glutathione Biosynthesis via Activation of the Nuclear Factor E2-Related Factor 2 (Nrf2)—Antioxidant-Response Element (ARE) Pathway Is Essential for Neuroprotective Effects of Sulforaphane and 6-(Methylsulfinyl) Hexyl Isothiocyanate"; J. Pharmacol. Sci., vol. 115, No. 3, Feb. 24, 2011, pp. 320-328 (9 pages).
Uto, T. et al.; "Molecular Mechanisms Underlying Anti-Inflammatory Actions of 6-(Methylsulfinyl) hexyl Isothiocyanate Derived from Wasabi (*Wasabia japonica*)"; Advances in Pharmacological Sciences, vol. 2012, Article ID 614046; 2012, pp. 1-9 (9 pages).
International Search Report issued in PCT/JP2016/079985 dated Nov. 8, 2016 (2 pages).
Written Opinion issued in PCT/JP2016/079985 dated Nov. 8, 2016 (8 pages).

\* cited by examiner

INHIBITOR OF MUSCLE DAMAGE OR MUSCLE FATIGUE

TECHNICAL FIELD

The present invention relates to a calpain activation inhibitor, muscle damage inhibitor, muscle endurance improver or muscle fatigue recovery agent containing an ω-methylsulfinylalkyl isothiocyanate or physiologically acceptable salt thereof as an active, foods or beverages, pharmaceuticals or cosmetics containing the same, a pharmaceutical for the prophylaxis and/or treatment of diseases related to muscle damage or diseases related to reduced muscle mass caused by aging, and a method for the use thereof.

BACKGROUND ART

In response to a growing trend towards health consciousness in recent years, an increasing number of persons are engaging in aerobic exercise training in order to eliminate obesity and other lifestyle diseases, and there is a growing understanding and awareness of recovery from muscle fatigue and other physiological effects on the body imparted by nutritional supplements taken before, during and after exercise training not only among athletes, but also members of the general public as well. In view of these circumstances, there is a desire for the development of supplements that support improvement of muscle endurance and recovery from muscle fatigue in order to efficiently engage in aerobic exercise training.

However, muscle damage or muscle fatigue caused by excessive exercise loading as well as diseases attributable thereto have only been treated using methods involving recuperation or simply waiting for muscle to recover while engaging in light exercise or rehabilitation, and drugs used for this purpose merely consisted of the use of anti-inflammatory drugs, analgesics and poultices for the purpose of symptomatic treatment.

Muscle dystrophy is the generic term for a hereditary disease presenting with symptoms mainly consisting of progressive muscle weakness and atrophy caused by degeneration and necrosis of muscle fibers, and is currently categorized into more than ten types based on its mode of inheritance and clinical characteristics, examples of which include Duchenne type, Becker type, limb-girdle type, congenital type, distal type, facioscapulohumeral type and myotonic type. Among these, the number of patients of the Duchenne type is largest, and research has been conventionally proceeded mainly on the Duchenne type.

At present, an effective treatment for muscular dystrophy has not yet to be found with the exception of steroid therapy, and the only benefit from steroid therapy is extension of the workable period of about two years. In addition, rehabilitation for the purpose of delaying progression of symptoms and respiratory care through the use of a ventilator are considered to have important significance at the present time.

Damage occurs to the sarcolemma when muscle is subjected to an excessive load brought on by exercise or other mechanical stress. When the sarcolemma is damaged, $Ca^{2+}$ present in extracellular fluid flows into the cells and is thought to accelerate the progression of muscle breakdown. Calpain-1 is known to be a proteolytic enzyme that is the key to the progression of muscle breakdown. Calpain-1 is a cysteine protease that is activated by $Ca^{2+}$, and activated calpain-1 causes muscle breakdown by limited decomposition of cytoskeletal proteins such as α-spectrin. Under normal physiological conditions, since activation of calpain-1 is inhibited by an endogenous inhibitor thereof in the form of calpastatin, muscle breakdown is considered to occur following the loss of inhibition of calpain-1 activation by calpastatin (Non-Patent Document 1).

The mdx mice, a model mouse of Duchenne muscular dystrophy are known to exhibit increased activation of calpain-1, and calpain-1 levels are known to be increased in the skeletal muscle of Duchenne patients. Consequently, calpain inhibitors are being developed as therapeutic drugs for Duchenne muscular dystrophy. For example, activation of calpain in muscle tissue and muscle breakdown have been reported to be inhibited as a result of administering leupeptin, which is a protease inhibitor known to have an inhibitory action on calpain, to mdx mice by intramuscular injection (Non-Patent Document 1). Although calpain inhibitors are continuing to be developed, their development is on the decline due to serious problems with toxicity and adverse side effects.

Sarcopenia is characterized by progressive and systemic reductions in skeletal muscle mass and skeletal muscle strength accompanying physical disabilities or decreases in quality of life caused by such factors as aging. Reduced muscle mass due to aging has been reported to be caused by muscle breakdown (Non-Patent Document 2).

6-methylsulfinylhexyl isothiocyanate (abbreviated as 6-MSITC) is a type of aromatic essence contained in Japanese horseradish (*Wasabia japonica*), and has been previously determined to have anti-oxidative and anti-inflammatory actions (Non-Patent Documents 3 and 4).

Patent Document 1 suggests that 6-methylsulfinylhexyl isothiocyanate can be used to decrease muscle-related diseases such as myopathy, muscle atrophy, myoglobinuria, hypotonia, muscle pain or exercise tolerance related to mitochondrial dysfunction by adjusting the NAD(P)+/NAD (P)H ratio as a result of activating NAD(P)H:quinone oxidoreductase (NQO1) (Patent Document 1).

Patent Document 2 describes that 6-methylsulfinylhexyl isothiocyanate inhibits the production of TNF-α, and suggests that it can be used to treat muscle-related diseases such as dermatomyositis or polymyositis (Patent Document 2).

Patent Document 3 describes that 6-methylsulfinylhexyl isothiocyanate inhibits increases in the concentration of adrenocorticotropic hormone (ACTH) in the blood as well as increases in blood cytokine and chemokine levels following mental or physical stress loading, and suggests that it can be used to treat muscle-related diseases such as dermatomyositis, myocarditis, fasciitis or myasthenia gravis (Patent Document 3).

However, ω-methylsulfinylalkyl isothiocyanate has previously not been known to have an inhibitory action on muscle damage caused by exercise loading by inhibiting activation of calpain-1.

PRIOR ART DOCUMENTS

Patent Documents

[Patent Document 1] Japanese Translation of PCT Application No. 2009-526839
[Patent Document 2] Japanese Unexamined Patent Publication No. 2009-132635
[Patent Document 3] Japanese Unexamined Patent Publication No. 2009-126826

Non-Patent Documents

[Non-Patent Document 1] Badalamente, M. A. and Stracher, A., Muscle Nerve., (23)1: 106-111 (2000)
[Non-Patent Document 2] Teixeira, Vivian de Oliveira Nunes, et al., Rev. Bras. Reumatol., 2012:52(2), 247-259
[Non-Patent Document 3] Mizuno, K., et al., J. Pharmacol. Sci., 115(3), 320-328 (2011)
[Non-Patent Document 4] Uto, T., et al., Adv. Pharmacol. Sci., 2012, 614046 (2012)

DISCLOSURE OF THE INVENTION

Problems to be Solved by the Invention

An object of the present invention is to provide a novel calpain activation inhibitor, muscle damage inhibitor, muscle endurance improver or muscle fatigue recovery agent, foods or beverages, pharmaceuticals or cosmetics containing the same, a pharmaceutical for the prophylaxis and/or treatment of diseases related to muscle damage or diseases related to reduced muscle mass caused by aging, and a method for the use thereof.

Means for Solving the Problems

As a result of conducting extensive studies to solve the aforementioned problems, the inventor of the present invention found that an ω-methylsulfinylalkyl isothiocyanate inhibits muscle damage by inhibiting activation of calpain, inhibits muscle damage in C57BL/6J mice following forced swimming exercise loading, and inhibits the progression of Duchenne muscular dystrophy in mdx mice, thereby leading to completion of the present invention.

Effects of the Invention

The present invention can provide a novel calpain activation inhibitor, muscle damage inhibitor, muscle endurance improver or muscle fatigue recovery agent containing an ω-methylsulfinylalkyl isothiocyanate or physiologically acceptable salt thereof as an active ingredient foods or beverages, pharmaceuticals or cosmetics containing the same, a pharmaceutical for the prophylaxis and/or treatment of diseases related to muscle damage or diseases related to reduced muscle mass caused by aging, and a method for the use thereof.

BEST MODE FOR CARRYING OUT THE INVENTION

The following provides a detailed explanation of the present invention.

<ω-Methylsulfinylalkyl Isothiocyanate>

In the present invention, an ω-methylsulfinylalkyl isothiocyanate may be a chemically synthesized substance or a naturally-occurring substance in the form of an extract obtained from a plant of the Brassicaceae family.

In the present invention, in the case the w-methylsulfinylalkyl isothiocyanate is a naturally-occurring substance, it can be obtained from one type or a plurality of types of plants selected from group consisting of members of the Brassicaceae family such as Japanese horseradish, horseradish, cabbage, watercress, Brussels sprouts, cauliflower, Japanese white radish, hot white radish, rapeseed, broccoli, leaf mustard, Indian mustard, turnip or Chinese cabbage, and is preferably obtained from Japanese horseradish (*Wasabia japonica*), which has a high content of 6-methylsulfinylhexyl isothiocyanate. Although the leaves and/or rhizomes, for example, of Japanese horseradish can be used, the rhizomes can be used preferably.

An example of a method used to prepare an ω-methylsulfinylalkyl isothiocyanate is as indicated below.

In the case of extracting an ω-methylsulfinylalkyl isothiocyanate from a plant of the Brassicaceae family containing an ω-methylsulfinylalkyl isothiocyanate, for example, although the plant body is preferably subjected to extraction pretreatment by the physical means of crushing or grating and then extracted with an organic solvent such as water, methanol, ethanol, acetone, ethyl acetate, diethyl ether, dichloromethane or dichloroethane, or is extracted using a distillation method such as steam distillation or molecular distillation, the method used is not particularly limited to these methods.

As a specific example of a method for extracting Japanese horseradish with an organic solvent, an ω-methylsulfinylalkyl isothiocyanate can be obtained by grating rhizomes of Japanese horseradish followed by extracting with ethyl acetate solvent, dehydrating the extract with anhydrous sodium sulfate, and concentrating with an evaporator. This method is particularly optimal for extracting 6-methylsulfinylhexyl isothiocyanate. A commercially available 6-methylsulfinylhexyl isothiocyanate may also be used, and an example thereof is Wasabisulfinyl® (6-MSITC®) manufactured by Kinjirushi Co., Ltd.

Japanese horseradish is extracted in the same manner in the case of extracting an w-methylsulfinylalkyl isothiocyanate from watercress, for example. For example, an ω-methylsulfinylalkyl isothiocyanate is obtained by grinding up the watercress followed by extracting with ethyl acetate solvent, dehydrating this extract with anhydrous sodium sulfate and concentrating with an evaporator. This method is particularly optimal for extracting 7-methylsulfinylheptyl isothiocyanate and 8-methylsulfinyloctyl isothiocyanate.

Furthermore, the aforementioned extracts can be purified by liquid-liquid distribution, chromatography, molecular distillation, refinement or other arbitrary method following extraction and concentration. A drying means such as a hot air dryer or freeze-dryer may be combined before and after the purification means.

In the present invention, examples of an ω-methylsulfinylalkyl isothiocyanates include allyl isothiocyanates, secondary butyl isothiocyanates, 3-butenyl isothiocyanate, 4-pentenyl isothiocyanate, 5-hexenyl isothiocyanate, 5-methylthiopentyl isothiocyanate, 6-methylthiohexyl isothiocyanate, 7-methylthioheptyl isothiocyanate and 8-methylthiooctyl isothiocyanate, and is preferably 6-methylthiohexyl isothiocyanate.

In the present invention, in addition to being extracted from a plant body according to the aforementioned methods, active ingredients other than the ω-methylsulfinylalkyl isothiocyanate can be synthesized by various types of chemical synthesis methods. A person with ordinary skill in the art would be able to synthesize these active ingredients according to methods commonly known in the art.

For example, ω-methylthioalkenol is obtained by refluxing with $CH_3$—SNa using ω-chloroalkenol for the starting substance followed by allowing $SOCl_2$ to act thereon to obtain ω-chloroalkenol methyl sulfide in accordance with the method of Kiaer, et al. (Kiaer, et al., Acta. Chem. Scand., 11, 1298, 1957).

Next, for example, an amino group is introduced to form N-(ω-methylthioalkyl)-phthalimide followed by the addition of hydrazine hydrate thereto and refluxing to obtain ω-methylthioalkylamine using the method of Gabriel, for example. Moreover, the methylthio group of ω-methylthioalkyl isothiocyanate, obtained by going through thiuram disulfide, is oxidized with mCPBA to obtain an ω-methylsulfinylalkyl isothiocyanate in accordance with the method of Li, et al. (Li, et al., J. Org. Chem., 62, 4539, 1997).

In the present invention, a "physiologically acceptable salt" refers to a salt that retains a physiological effect or retains the physiological properties of a free base or free acid or that which is not undesirable for other reasons. In the present invention, examples of physiologically acceptable salts include pharmaceutically acceptable salts.

<Calpain Activation Inhibitor and the Like>

The present invention relates to a calpain activation inhibitor containing an ω-methylsulfinylalkyl isothiocyanate or a physiologically acceptable salt thereof as an active ingredient and is also referred to as a calpain-1 activation inhibitor or calpain inhibitor.

The calpain activation inhibitor and the like of the present invention is able to inhibit the release of substances such as creatine phosphokinase (CPK), lactate dehydrogenase (LDH), myoglobin (Mb), aspartate transferase (AST), alanine aminotransferase (ALT) or aldolase (ALD) into the blood, which is caused by exercise loading, by inhibiting activation of calpain.

The calpain activation inhibitor and the like of the present invention is able to inhibit the release of substances such as creatine phosphokinase (CPK), lactate dehydrogenase (LDH), myoglobin (Mb), aspartate transferase (AST), alanine aminotransferase (ALT) or aldolase (ALD) into the blood, which is caused by degradation of muscle protein, by inhibiting activation of calpain.

The calpain activation inhibitor and the like of the present invention is able to inhibit the release of substances such as creatine phosphokinase (CPK), lactate dehydrogenase (LDH), myoglobin (Mb), aspartate transferase (AST), alanine aminotransferase (ALT) or aldolase (ALD) into the blood as a result of stabilizing muscle by inhibiting activation of calpain.

<Muscle Damage Inhibitor and the Like>

The present invention relates to a muscle damage inhibitor, muscle breakdown inhibitor, muscle protein degradation inhibitor, muscle stabilizer, muscle endurance improver and muscle fatigue recovery agent containing an ω-methylsulfinylalkyl isothiocyanate or a physiologically acceptable salt thereof as an active ingredient, and these may also be referred to as a muscle damage inhibitor and the like.

The muscle damage inhibitor and the like of the present invention are able to inhibit the release of substances such as creatine phosphokinase (CPK), lactate dehydrogenase (LDH), myoglobin (Mb), aspartate transferase (AST), alanine aminotransferase (ALT) or aldolase (ALD) caused by exercise loading into the blood.

The muscle damage inhibitor and the like of the present invention are able to inhibit the release of substances such as creatine phosphokinase (CPK), lactate dehydrogenase (LDH), myoglobin (Mb), aspartate transferase (AST), alanine aminotransferase (ALT) or aldolase (ALD) caused by activation of calpain and a deficit of dystrophin into the blood.

The muscle damage inhibitor and the like of the present invention are able to inhibit the release of substances such as creatine phosphokinase (CPK), lactate dehydrogenase (LDH), myoglobin (Mb), aspartate transferase (AST), alanine aminotransferase (ALT) or aldolase (ALD) caused by muscle protein degradation into the blood.

The muscle damage inhibitor and the like of the present invention are able to inhibit the release of substances such as creatine phosphokinase (CPK), lactate dehydrogenase (LDH), myoglobin (Mb), aspartate transferase (AST), alanine aminotransferase (ALT) or aldolase (ALD) into the blood as a result of stabilizing muscle by inhibiting activation of calpain.

<Foods or Beverages (Foods with Function Claims, Foods for Specified Health Uses), Pharmaceuticals and Cosmetics Containing Muscle Damage Inhibitor and the Like as an Active Ingredient and/or Additive>

The muscle damage inhibitor and the like of the present invention can be contained in foods or beverages (foods with function claims, foods for specified health uses), pharmaceuticals and cosmetics. In addition, one aspect of the present invention is foods or beverages (food with function claims, food for specified health uses), pharmaceuticals or cosmetics containing the muscle damage inhibitor and the like as an active ingredient and/or additive thereof. A preferable aspect of the present invention is an orally administered pharmaceutical (including orally administered quasi-drugs) and foods or beverages containing the muscle damage inhibitor and the like of the present invention.

In the case of containing the muscle damage inhibitor and the like of the present invention in a food or beverage, the food or beverage may be prepared in a desired form by mixing in a sweetener, food coloring, preservative, thickener, stabilizer, gelling agent, sizing agent, antioxidant, coloring agent, bleaching agent, antifungal agent (anti-mold agent), yeast food, gum base, fragrance, souring agent, flavor enhancer, emulsifier, pH adjuster, brine, leavening agent, nutrient enriching agent or other food or beverage material in addition to the muscle damage inhibitor and the like of the present invention. There are no particular limitations on the form of the food or beverage containing the muscle damage inhibitor and the like of the present invention. Examples thereof include supplement type foods such as gels, granules, grains, capsules, tablets, powders, liquids or semi-solids, beverages such as carbonated beverages, soft drinks, milk-based beverages, alcoholic beverages, fruit-based beverages, teas or nutrient drinks, powdered beverages such as powdered juice or powdered soup, confections such as chewing gum, tablets, candy, cookies, gumdrops, rice crackers, biscuits or jelly, as well as bread, noodles, cereal, jam and condiments. These foods can be used as, for example, ordinary foods or beverages as well as neutraceuticals such as nutritional supplements, functional foods, foods for specified health uses, or foods for invalids. These foods or beverages are used as foods or beverages for inhibiting muscle damage, for example.

In the case of containing the muscle damage inhibitor and the like of the present invention in a pharmaceutical (including quasi-drugs), other pharmaceutically effective ingredients, pharmaceutically acceptable carriers or additives and the like may be contained as necessary in addition to the muscle damage inhibitor and the like of the present invention. Examples of pharmaceutically acceptable carriers and additives include binders, disintegration agents, lubricants, wetting agents, buffers, preservatives and fragrances. There are no particular limitations on the form of a pharmaceutical containing the muscle damage inhibitor and the like of the present invention. Examples of drug forms include injections, external preparations, inhalants, suppositories, films, troches, liquids, powders, tablets, granules, capsules, syrups, eye drops, eye washes and nose drops. In addition, a form suitable for oral administration (namely, an orally administered pharmaceutical) is preferable, and examples thereof include troches, liquids, powders, tablets, granules, capsules and syrups. These pharmaceuticals (including quasi-drugs) are used as pharmaceuticals for inhibiting muscle damage and the like.

In the case of containing the muscle damage inhibitor and the like of the present invention in a cosmetic (including functional cosmetics) or quasi-drug for external use, a pharmaceutically or cosmetologically acceptable carrier (such as water or an oily component) can be contained in addition to the muscle damage inhibitor and the like of the present invention and prepared in a desired form. There are no particular limitations on the form of the cosmetic provided it can be applied to the skin. Examples of cosmetic forms include liquids, milky lotions, powders, solids, suspensions, creams, ointments, mousses, granules, tablets, gels, jellies, pastes, gelatins, aerosols, sprays, liniments and packs. These cosmetics are used as cosmetics having an inhibitory action on muscle damage, for example.

Moreover, the muscle damage inhibitor and the like of the present invention can also be used as an active ingredient and/or additive of a food or beverage, pharmaceutical (including quasi-drugs) or cosmetic, and according to a food or beverage, pharmaceutical (including quasi-drugs) or cosmetic containing the muscle damage inhibitor and the like of the present invention, an effect by the muscle damage inhibitor and the like of the present invention is obtained. As a result of containing the muscle damage inhibitor and the like of the present invention in a food or beverage, pharmaceutical (including quasi-drugs) or cosmetic, the action of inhibiting muscle damage can be imparted. The muscle damage inhibitor and the like of the present invention can be used to impart the function of inhibiting muscle damage and the like to an orally administered pharmaceutical (including orally administered quasi-drugs) or food or beverage.

In the case of using the muscle damage inhibitor and the like of the present invention as an additive as well, there are no particular limitations on the form of the food or beverage, pharmaceutical (including quasi-drugs) or cosmetic in which it is contained, and examples thereof include the previously described food or beverage, pharmaceutical (including quasi-drugs) and cosmetic forms.

There are no particular limitations on the amount of the muscle damage inhibitor and the like of the present invention contained in a food or beverage, pharmaceutical (including quasi-drugs) or cosmetic, and is suitably set corresponding to the objective of application (such as the type of target disease or symptoms), application target site, gender and age of the subject, form of the food or beverage, pharmaceutical (including quasi-drugs) or cosmetic, administration or ingestion method and number of administrations thereof or preference. Thus, although there are no particular limitations on the contained amount of the muscle damage inhibitor and the like of the present invention in a food or beverage, pharmaceutical (including quasi-drugs) or cosmetic, the daily adult dosage of the muscle damage inhibitor and the like of the present invention is, for example, such that aforementioned an ω-methylsulfinylalkyl isothiocyanate is contained so that the total amount thereof is 0.1 mg to 100 mg, preferably 0.1 mg to 70 mg, more preferably 0.5 mg to 50 mg and particularly preferably 0.5 mg to 30 mg. In addition, as was previously described, in addition to the aforementioned an ω-methylsulfinylalkyl isothiocyanate being obtained by subjecting a plant of the Brassicaceae family, such as Japanese horseradish, horseradish, cabbage, watercress, Brussels sprouts, cauliflower, Japanese white radish, hot white radish, rapeseed, broccoli, leaf mustard, Indian mustard, turnip or Chinese cabbage, to extraction and purification treatment, these components can also be obtained from a plant by subjecting to extraction and purification treatment, and an extract per se obtained in this process may be used as the muscle damage inhibitor and the like of the present invention, and in the case of using this extract per se as the muscle damage inhibitor and the like of the present invention, it is preferably contained in a food or beverage, pharmaceutical (including quasi-drugs) or cosmetic at a daily adult dosage within the range of 0.01 g to 1.0 g, preferably 0.01 g to 0.7 g, more preferably 0.05 g to 0.5 g, and particularly preferably 0.05 g to 0.3 g.

<Composition>

The present invention also relates to a composition containing an ω-methylsulfinylalkyl isothiocyanate or a physiologically acceptable salt as an active ingredient thereof. The explanation of foods or beverages, pharmaceuticals or cosmetics of the present invention is applicable to a food or beverage, pharmaceutical or cosmetic composition of the present invention.

The food or beverage, pharmaceutical or cosmetic composition of the present invention contains an ω-methylsulfinylalkyl isothiocyanate or a physiologically acceptable salt thereof at, for example, 0.00050% by weight to 0.425% by weight, and preferably 0.0025% by weight to 0.40% by weight, based on a value of 100% by weight for the total weight of the composition.

The food or beverage, pharmaceutical or cosmetic composition of the present invention contains, for example, 0.1% by weight to 85.0% by weight, and preferably 0.5% by weight to 80.0% by weight, of a plant extract containing an ω-methylsulfinylalkyl isothiocyanate or a physiologically acceptable salt thereof based on a value of 100% by weight for the total weight of the composition.

The food or beverage, pharmaceutical or cosmetic composition of the present invention contains, for example, 15.0% by weight to 99.9% by weight, and preferably 20.0% by weight to 99.5% by weight, of a physiologically acceptable additive based on a value of 100% by weight for the total weight of the composition.

There are no particular limitations on the additive in the food or beverage, pharmaceutical or cosmetic composition of the present invention provided it is a physiologically inert, inorganic or organic additive. An additive such as lactic acid, cornstarch or derivative thereof, talc, stearic acid or salt thereof, oligosaccharide, HPMC, titanium oxide, reduced maltose syrup, edible purified processed oils and fats, vitamin C, cellulose, fragrance, cyclodextrin, citric acid or vitamin B12 can be used as such an additive for a tablet, sugar-coated tablet or hard gelatin capsule, for example. Examples of suitable additives for soft gelatin capsules include vegetable oils, waxes, fats and semi-solid or liquid polyols. Examples of suitable additives for liquids or syrups include water, polyols, sucrose, inverted sugars and glucose. Examples of additives suitable for injection preparations include water, alcohols, polyols, glycerol and vegetable oils. Examples of additives suitable for suppositories include natural or hydrogenated oils, waxes, fats and semi-liquid or liquid polyols.

<Use>

The muscle damage inhibitor and the like, calpain activation inhibitor, food or beverage, pharmaceutical or cosmetic, and food or beverage, pharmaceutical or cosmetic composition of the present invention can be used indicated below.

In the present invention, "inhibition of muscle damage" refers to inhibiting an increase in the blood concentration of muscle damage indicators such as serum myoglobin or CPK following exercise. Indicators such as CPK (creatine phosphokinase) are enzymes contained in muscle cells that are released into the blood when muscle damage has occurred, after which the blood concentrations thereof decrease accompanying recovery. Thus, measurement of these muscle damage indicators such as CPK can be used as an indicator of muscle damage.

In the present invention, "recovery from muscle damage" refers to returning of the blood concentrations of indicators of muscle damage such as serum myoglobin or CPK following exercise to normal levels. Indicators such as CPK (creatine phosphokinase) are enzymes contained in muscle cells that are released into the blood when muscle damage has occurred, and the blood concentrations thereof decrease accompanying recovery. Thus, measurement of indicators such as CPK can be used as an indicator of muscle damage.

In the present invention, "recovery from muscle fatigue" refers to improvement of a state in which phosphoric acid (derived from ATP or creatine phosphate and the like) produced by exercise accumulates and binds with calcium, thereby exacerbating the function of calcium essential for muscle contraction.

In the present invention, "stabilization of muscle" refers to inhibiting the fusion, degradation and fragmentation of the proteins of muscle fibers.

In the present invention, "improvement of muscle quality" refers to the formation of muscle that is resistant to the occurrence of muscle damage or muscle breakdown caused by exercise loading.

In the present invention, examples of diseases related to muscle damage, and especially diseases related to muscle damage caused by exercise loading, include delayed onset muscle soreness and muscular dystrophy. Examples of muscular dystrophy include Duchenne type, Becker type, limb-girdle type, congenital type, distal type, facioscapulohumeral type and myotonic type, preferably include Duchenne type, Becker type, congenital type, limb-girdle type and myotonic type, and more preferably include Duchenne type. Examples of applications of the present invention include the prophylaxis and/or treatment of diseases related to muscle damage.

In the present invention, an example of a disease related to reduced muscle mass caused by aging is sarcopenia. Examples of applications of the present invention include prophylaxis and/or treatment of diseases related to reduced muscle mass caused by aging.

In the present invention, statements such as "relieves temporary physical fatigue during the course of daily life", "relieves physical fatigue occurring during exercise", "useful in maintaining muscle health", "strengthens muscle", "maintains muscle", "fortifies muscle", "maintains declining walking ability due to aging in the middle-aged and elderly", "supports strength for muscle development", "supports strength for developing muscle useful for maintaining declining muscle strength caused by aging" or "improves walking ability", or statements similar thereto, can be displayed on products relating to the muscle damage inhibitor of the present invention, product information or product advertisements (such as transaction documents, usage instructions, product inserts, or catalogs and Internet web sites used for mail-order sales).

<Other Aspects>

The present invention includes the aspects indicate below and the aforementioned explanations can be cited therein.

The present invention relates to an ω-methylsulfinylalkyl isothiocyanate or physiologically acceptable salt thereof for use in inhibiting calpain activation, inhibiting muscle damage, improving muscle endurance, recovering from muscle fatigue, the prophylaxis and/or treatment of diseases and/or symptoms related to muscle damage caused by exercise loading, the prophylaxis and/or treatment of diseases and/or symptoms related to reduced muscle mass caused by aging, and the prophylaxis and/or treatment of muscular dystrophy or sarcopenia.

The present invention also relates to a method for inhibiting calpain activation, a method for inhibiting muscle damage, a method for improving muscle endurance, a method for recovering from muscle fatigue, a method for the prophylaxis and/or treatment of diseases and/or symptoms of muscle damage caused by exercise loading, a method for the prophylaxis and/or treatment of diseases and/or symptoms related to reduced muscle mass caused by aging, and a method for the prophylaxis and/or treatment of muscular dystrophy or sarcopenia by administering an effective amount of an ω-methylsulfinylalkyl isothiocyanate or physiologically acceptable salt thereof to a subject. The subject is, for example, a mammal, and is preferably a human.

The present invention also relates to a use of an ω-methylsulfinylalkyl isothiocyanate or physiologically acceptable salt thereof for the manufacture of a pharmaceutical, cosmetic or food or beverage for inhibiting calpain activation, inhibiting muscle damage, improving muscle endurance, recovering from muscle fatigue, the prophylaxis and/or treatment of diseases and/or symptoms related to muscle damage caused by exercise loading, the prophylaxis and/or treatment of diseases and/or symptoms related to reduced muscle mass caused by aging, and the prophylaxis and/or treatment of muscular dystrophy or sarcopenia.

Although the following provides an explanation of the present invention by indicating examples and preparation examples thereof, the present invention is not limited to these examples and preparation examples.

Example 1

Example 1: Effect of Inhibiting Calpain-1 Activation by 6-MSITC Contained in Japanese Horseradish C57/BL10-mdx mice were used as a disease model of Duchenne type muscular dystrophy. The mice were housed using a light-dark cycle, during which the room was illuminated from 8:00 to 22:00, and given free access to feed and water. The mdx mice were allowed to self-breed, and 4-week-old female mdx mice were administered 125.1 ppm of 6-MSITC mixed in drinking water for 4 weeks. Mice of a control group were allowed to drink water only. After isolating the gastrocnemius, RIPA buffer (Nacalai Tesque, Inc., Catalog No. 08714-04) containing a protease inhibitor cocktail was added in amount equal to 50 times muscle weight followed by homogenizing with the Biomasher SP (Nippi, Inc.). After homogenizing, the mixture was incubated for 30 minutes on ice followed by centrifuging for 10 minutes at 16,000 rpm and 4° C. and recovering the supernatant. Protein assay was carried out with the Pierce BCA Protein Assay Kit (Thermo Fisher Scientific, Inc., Catalog No. 23227). Following the protein assay, sample buffer was added followed by incubating for 5 minutes at 95° C. and using the resulting muscle extract as a sample for western blotting. SDS-PAGE was then carried out in gel at a concentration gradient of 7.5% or 4% to 20% to separate the protein. After transferring the membrane, the membrane was washed (5 minutes×3 times), blocked for 1 hour with 5% skim milk, washed again (10 minutes×2.5 minutes×1 time), and then reacted overnight at 4° C. using primary antibodies consisting of Calpain-1 Large Subunit Antibody (dilution factor: 1:1000, Cell Signaling Technology, Inc., Catalog No. 2556), calpastatin antibody (dilution factor: 1:1000, Cell Signaling Technology, Inc., Catalog No. 4146), and β-actin antibody (dilution factor: 1:1000, Cell Signaling Technology, Inc., Catalog No. 4967). After reacting with primary antibody, the membrane was washed (10 minutes×2.5 minutes×1 time) and then reacted for 1 hour at room temperature using secondary antibody consisting of ECL-anti-rabbit IgG HRP antibody (dilution factor: 1:10000, GE Healthcare, Inc., Catalog No. LNA934V/AG). After washing (10 minutes×2.5 minutes×1 time), the membrane was reacted with ECL Prime Detection Reagent (GE Healthcare, Inc., Catalog No. RPN2236) and bands were detected with the FPM100 Fuji Medical Film Processor.

Figure 1:
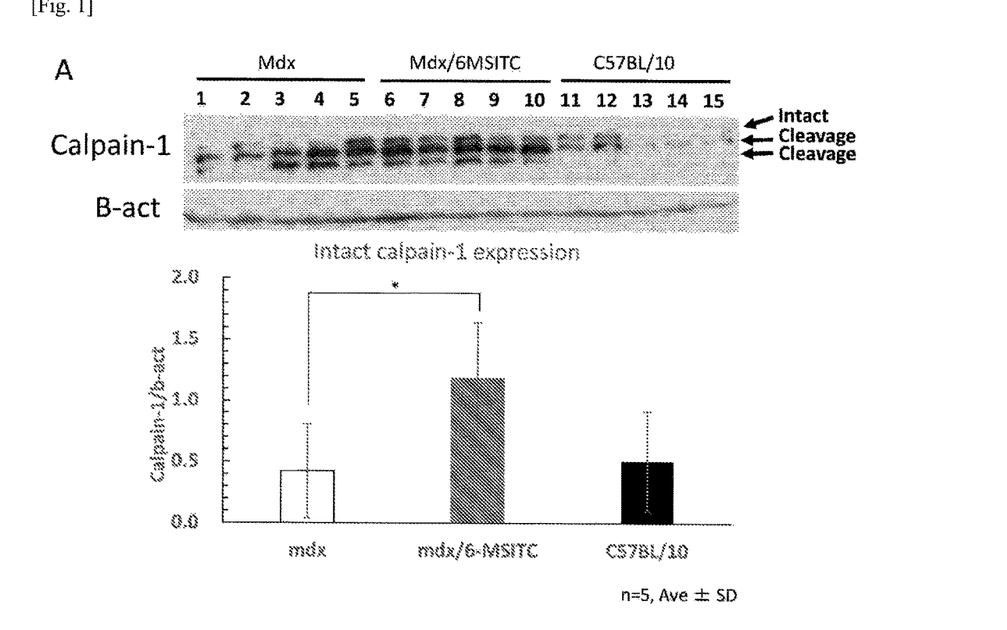
FIG. 1 indicates the effect of 6-MSITC of inhibiting activation of calpain-1.
Figure 2:
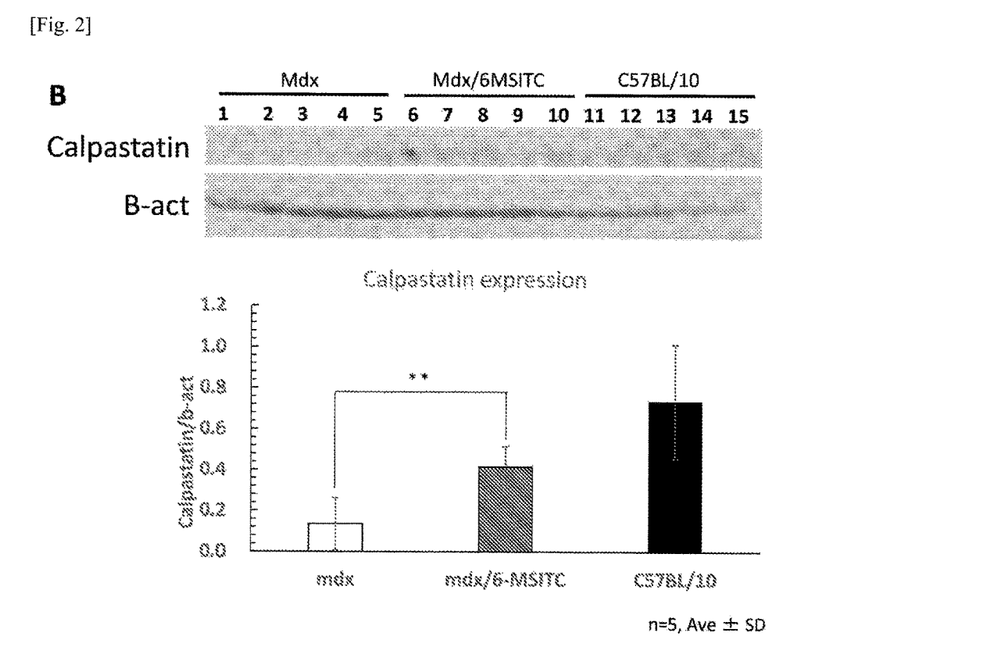
FIG. 2 indicates the effect of 6-MSITC of suppressing expression of calpastatin.
Figure 3:
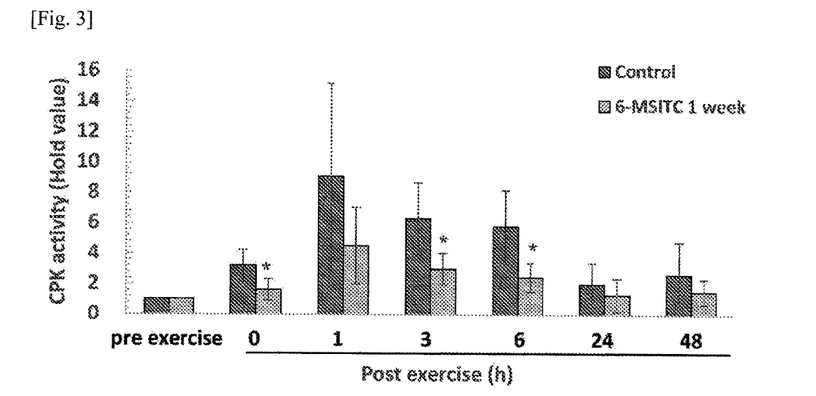
FIG. 3 indicates the effect of 6-MSITC of inhibiting muscle damage using blood CPK levels following forced swimming exercise loading as an indicator (after administering for 1 week).
Figure 4:
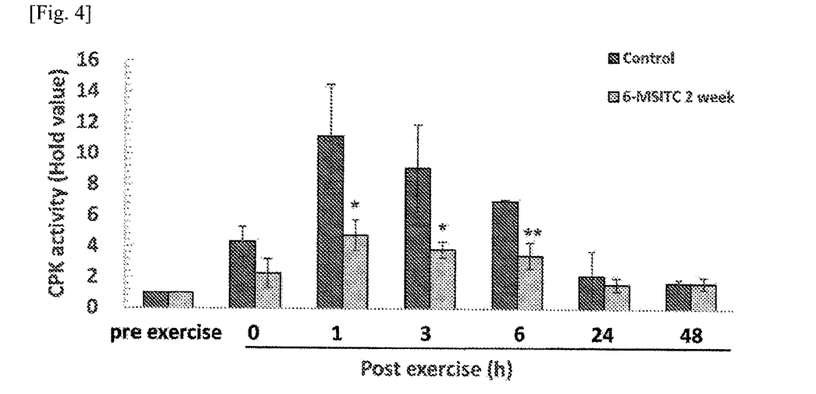
FIG. 4 indicates the effect of 6-MSITC of inhibiting muscle damage using blood CPK levels following forced swimming exercise loading as an indicator (after administering for 2 weeks).
Figure 5:
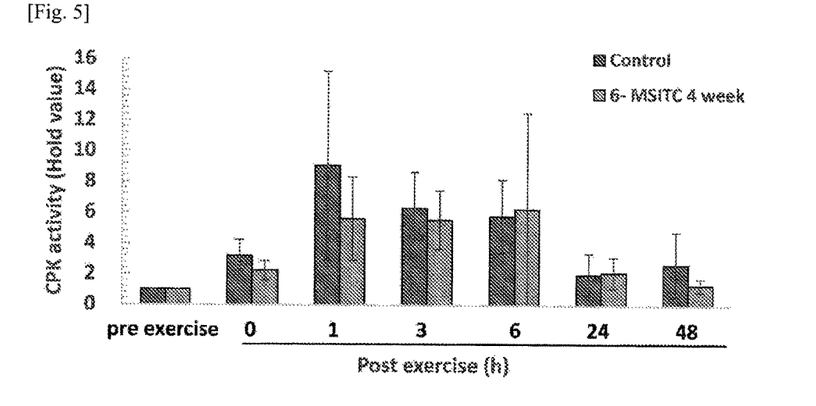
FIG. 5 indicates the effect of 6-MSITC of inhibiting muscle damage using blood CPK levels following forced swimming exercise loading as an indicator (after administering for 4 weeks).
Figure 6:
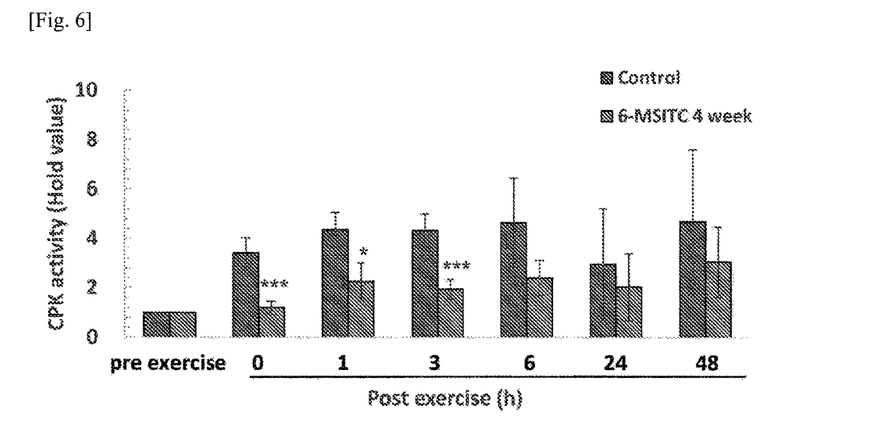
FIG. 6 indicates the effect of 6-MSITC of inhibiting muscle damage using blood CPK levels following forced swimming exercise loading as an indicator (after administering for 1 week).

When activation of calpain-1 in the gastrocnemius extract was evaluating according to the band pattern obtained by western blotting, a comparison between the mdx/control group and mdx/6-MSITC group revealed that a significant amount of full-length (intact) calpain-1 remained and a reduction in cleavage bands in the mdx/6-MSITC group was observed as shown in FIG. 1. This indicates that activation of calpain-1 is inhibited (p=0.020) by administration of 6-MSITC. In order to evaluate whether activation of calpain-1 suppresses muscle breakdown, the expression level of calpastatin, an endogenous calpain-1 inhibitor, was evaluated. As shown in FIG. 2, when a comparison was made between the mdx/control group and mdx/6-MSITC group, a large amount of calpastatin remained in the mdx/6-MSITC group (p=0.0049). This result indicates that calpain-1 does not decompose the substrate. Accordingly, 6-MSITC was indicated to inhibit muscle breakdown by inhibiting activation of calpain-1 in muscle tissue as a result of inhibiting activation of calpain-1 and calpastatin remaining therein. Furthermore, tests for statistical significance were conducted between the mdx/control group and mdx/6-MSITC group using the Student's t-test. Levels of statistical significance consisted of *: $p<0.05$ and **: $p<0.01$.

Example 2

Figure 7:
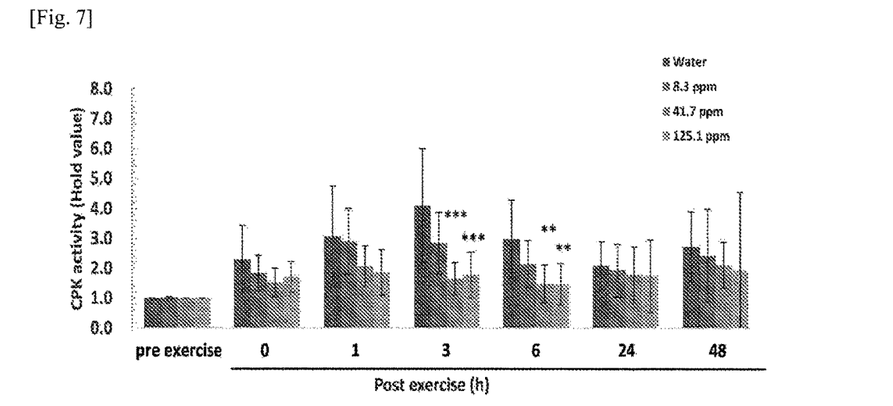
FIG. 7 indicates the dose-dependent effect of 6-MSITC of inhibiting muscle damage using blood CPK levels following forced swimming exercise loading as an indicator (after administering for 4 weeks).

Example 2: Effect of 6-MSITC Contained in Japanese Horseradish of Inhibiting Muscle Damage Caused by Forced Swimming Exercise After purchasing 4-week-old male C57BL/6J mice (Charles River Laboratories Japan, Inc.), an acclimation period was provided for a minimum of one week. The mice were housed using a light-dark cycle, during which the room was illuminated from 8:00 to 22:00, and given free access to feed and water. 6-MSITC was administered by mixing into drinking water at 41.7 ppm starting at age 8 weeks for a 1 week dose group, at age 7 weeks for a 2 week dose group, and at age 5 weeks for a 4 week dose group. Mice of a control group were allowed to drink water only. Body weights were measured once a week. The mice, having a weight equal to 10% of their body weight attached to their tail, were placed in a cylindrical tube having a diameter of about 14 cm filled with water at 25° C. to 27° C. to a depth of 13 cm after administering 6-MSITC for 1, 2 or 4 weeks and subjected to forced swimming exercise for 2.5 minutes. Blood was collected over time from the caudal vein of the mice using a heparinized capillary tube immediately after and 1, 3, 6, 24 and 48 hours after forced swimming exercise, and using the plasma obtained after centrifuging for 15 minutes at 3,000×g and 4° C. for measurement. Blood collected 2 to 3 hours prior to forced swimming exercise was used to provide steady-state values. A deviation enzyme in the form of CPK was measured with the Fuji Dri-Chem System (Fuji Film Corp., Model Dri-Chem 3500V) using the CPK-PIII Fuji Dri-Chem Slide (Fuji Film Corp.) as an indicator of muscle damage. The effects of 6-MSITC of inhibiting muscle damage using blood CPK values as an indicator following forced swimming exercise loading are shown in Tables 1 and 2 and FIGS. 3 to 7. As shown in Tables 1 and 2 and FIGS. 3 to 7, in comparison with the rate of rise of CPK values in the control group (water only) following forced swimming exercise loading, the rate of rise in CPK values was inhibited in the 6-MSITC dose group. Inhibition of the rate of rise in CPK values was observed in each of the 1 week, 2 week and 4 week dose groups. The results of testing the dose-dependency of the effect of 6-MSITC on muscle damage following forced swimming exercise loading are shown in FIG. 7. As is shown in FIG. 7, dose-dependent inhibition of CPK secretion was observed 3 and 6 hours after forced swimming. Furthermore, tests for statistical significance were conducted between the control group and 6-MSITC groups at each time using Dunnett's test. Levels of statistical significance consisted of *: $p<0.05$, : $p<0.01$ and *: $p<0.001$.

TABLE 1

|  | Pre-exercise | 0 h | 1 h | 3 h | 6 h | 24 h | 48 h |
|---|---|---|---|---|---|---|---|
| Control | 158 ± 37 | 487 ± 129 | 1282 ± 561 | 945 ± 203 | 867 ± 217 | 297 ± 181 | 442 ± 385 |
| 1 week dose group | 250 ± 111 | 368 ± 153 | 986 ± 337 | 691 ± 237 | 537 ± 129 | 248 ± 89 | 319 ± 125 |
| Control | 92 ± 4 | 394 ± 90 | 1020 ± 297 | 838 ± 276 | 638 ± 36 | 203 ± 158 | 159 ± 26 |
| 2 week dose group | 152 ± 29 | 335 ± 114 | 708 ± 85 | 571 ± 34 | 516 ± 89 | 170 ± 25 | 181 ± 23 |
| Control | 158 ± 37 | 487 ± 129 | 1282 ± 561 | 945 ± 203 | 867 ± 217 | 297 ± 181 | 442 ± 385 |
| 4 week dose group | 137 ± 44 | 319 ± 98 | 1044 ± 696 | 894 ± 392 | 772 ± 503 | 171 ± 163 | 186 ± 48 |

TABLE 2

|  | Pre-exercise | 0 h | 1 h | 3 h | 6 h | 24 h | 48 h |
|---|---|---|---|---|---|---|---|
| Control | 98 ± 22 | 343 ± 130 | 430 ± 137 | 442 ± 108 | 486 ± 276 | 257 ± 124 | 420 ± 166 |
| 6-MSITC 4 week dose group | 141 ± 28 | 164 ± 11 | 303 ± 59 | 267 ± 32 | 324 ± 50 | 272 ± 181 | 438 ± 227 |

Example 3

Example 3: Endurance Improving Effect of 6-MSITC Contained in Japanese Horseradish on Duchenne Type Muscular Dystrophy After purchasing 8-week-old male and female C57BL/10-mdx mice (Central Institute for Experimental Animals), mice were used that were born during the course of self-breeding. The mice were housed using a light-dark cycle, during which the room was illuminated from 8:00 to 22:00, and given free access to feed and water. Mice of the 6-MSITC dose group were administered 125.1 ppm of 6-MSITC mixed with water based on results for the effect of inhibition of exercise-induced muscle damage, while mice of a control group were allowed to drink water. The control group was given water only.

In an endurance evaluation test 1 (running uphill), 5-week-old male C57BL/10-mdx mice were administered 125.1 ppm of 6-MSITC mixed with water. Body weights were measured once a week. A treadmill running load test was conducted 9 weeks after administration of 6-MSITC. The Model TMW-2 manufactured by Melquest Ltd. was used in the treadmill running test. After warming up for 5 minutes at 3 m/min, a running load test was conducted for 10 minutes at 15 m/min. The running load test was conducted at an incline of +15°.

In an endurance evaluation test 2 (running downhill), 4-week-old male C57BL/10-mdx mice were administered 125.1 ppm of 6-MSITC mixed with water. Body weights were measured once a week. A treadmill running load test was conducted 4 and 8 weeks after administration of 6-MSITC. The Model TMW-2 manufactured by Melquest Ltd. was used in the treadmill running test. After warming up for 5 minutes at 5 m/min, the speed was increased from 5 m/min to 22 m/min over the course of 5 to 8 minutes after which the mice were made to run for 30 minutes at 22 m/min. This running load test was conducted at an incline of −15°.

The effects of 6-MSITC of improving endurance in endurance evaluation test 1 (running uphill) are shown in Table 3. All of the individuals of the 6-MSITC dose groups were able to run uphill for 10 minutes and improvement of endurance was observed.

Figure 8:
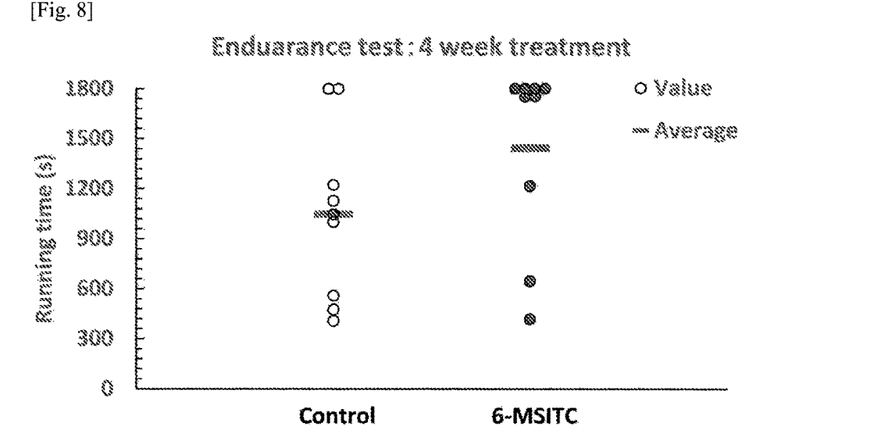
FIG. 8 indicates the inhibitory effect of 6-MSITC on the progression of Duchenne muscular dystrophy (after administering for 4 weeks).
Figure 9:
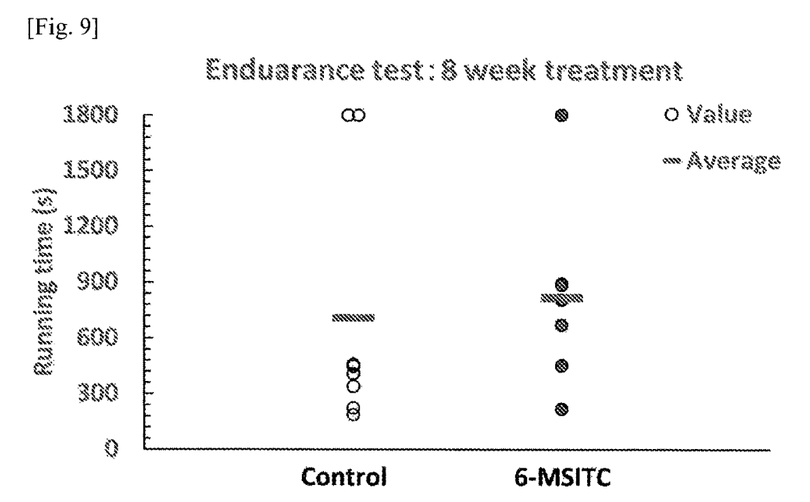
FIG. 9 indicates the inhibitory effect of 6-MSITC on the progression of Duchenne muscular dystrophy (after administering for 8 weeks).

The effects of 6-MSITC of improving endurance in endurance evaluation test 2 (running downhill) are shown in FIGS. 8 and 9. There were no significant differences observed in maximum running times in either of the 4 week and 8 week dose groups, and decreases in maximum running times were observed with age. However, although significant differences were not observed between the control group and 6-MSITC dose groups, when considering the individual running times of mice in the control group and 6-MSITC groups, administration of 6-MSITC was indicated to extend maximum running time (see FIGS. 8 and 9).

TABLE 3

|  | No. of mice able to run for 10 minutes (5 mice per group) |
|---|---|
| Control | 1 |
| 6-MSITC 9 week dose group | 5 |

Example 4

Example 4: Muscle Damage Inhibitory Effect of 6-MSITC Contained in Japanese Horseradish on Duchenne Type Muscular Dystrophy After purchasing 8-week-old male and female C57BL/10-mdx mice (Central Institute for Experimental Animals), mice were used that were born during the course of self-breeding. Male C57BL10 mice purchased from Japan SLC, Inc. were used a non-disease model control. The mice were housed using a light-dark cycle, during which the room was illuminated from 8:00 to 22:00, and given free access to feed and water. Mice of the 6-MSITC dose group were administered 125.1 ppm of 6-MSITC mixed with water based on results for the effect of inhibition of exercise-induced muscle damage. Four-week-old mice of the mdx dose group were administered 125.1 ppm of 6-MSITC mixed with water.

Figure 10:
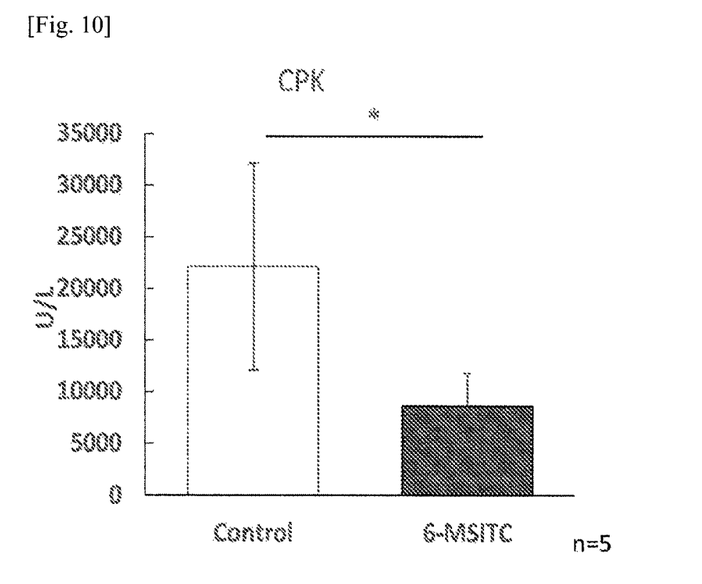
FIG. 10 indicates the effect of 6-MSITC of inhibiting muscle damage using blood CPK levels as an indicator in Duchenne muscular dystrophy model mice.

Mice of the control group were given water only. Cardiac blood was collected 4 hours after the start of administration of 6-MSITC and plasma obtained after centrifuging for 15 minutes at 3,000×g and 4° C. was used for measurement. The deviation enzyme, CPK, was measured with the Fuji Dri-Chem System (Fuji Film Corp., Model Dri-Chem 3500V) using the CPK-PIII Fuji Dri-Chem Slide (Fuji Film Corp.) as an indicator of muscle damage. The effects of 6-MSITC of inhibiting muscle damage in Duchenne type muscular dystrophy using blood CPK values as an indicator are shown in FIG. 10. As shown in FIG. 10, blood CPK values decreased in the 6-MTISC dose group. Furthermore, testing for statistical significance was conducted between the control group and the 6-MSITC group at each time using Student's t-test. The level of statistical significance was *: $p<0.05$.

FORMULATION EXAMPLES

Formulation Example 1: Capsule Preparation

| | |
|---|---|
| Japanese horseradish extract/oligosaccharide | 79 wt % |
| Calcium stearate | 3 wt % |
| HPMC/titanium oxide | 18 wt % |

A composition (330 mg) obtained by mixing the aforementioned ingredients was sealed in a capsule to produce a capsule preparation.

Formulation Example 2: Tablet Preparation

| | |
|---|---|
| Japanese horseradish extract/oligosaccharide | 0.9 wt % |
| Reduced maltose syrup | 55 wt % |
| Edible purified processed oils and fats | 4.0 wt % |
| Vitamin C | 24 wt % |
| Cellulose | 10 wt % |
| Fragrance | 2.0 wt % |
| Calcium stearate | 1.5 wt % |
| Cyclodextrin | 1.4 wt % |
| Citric acid | 1.0 wt % |
| Vitamin B12 | 0.2 wt % |

A composition (330 mg/tablet) obtained by mixing the aforementioned ingredients was molded into a tablet to produce a tablet preparation.

INDUSTRIAL APPLICABILITY

The present invention is able to provide a calpain activation inhibitor, muscle damage inhibitor, muscle endurance improver or muscle fatigue recovery agent containing an ω-methylsulfinylalkyl isothiocyanate or physiologically acceptable salt thereof as an active ingredient, foods or beverages, pharmaceuticals or cosmetics containing the same, a pharmaceutical for the prophylaxis and/or treatment of diseases related to muscle damage or diseases related to reduced muscle mass caused by aging, and a method for the use thereof.

The invention claimed is:

1. A method of treating Duchenne type muscular dystrophy, comprising administering an effective amount of 6-methylsulfinylhexyl isothiocyanate or physiologically acceptable salt thereof to a subject having Duchenne type muscular dystrophy.

2. The method according to claim 1, wherein the subject has muscle damage.

3. The method according to claim 1, wherein muscle damage is suppressed in the subject after the administration.

4. The method according to claim 1, wherein the muscular dystrophy is suppressed in the subject after the administration.

* * * * *